United States Patent [19]
Moy

[11] Patent Number: 5,509,909
[45] Date of Patent: Apr. 23, 1996

[54] BENT CHEST TUBE ASSEMBLY

[76] Inventor: Grant G. Moy, 890 Jackson St., San Francisco, Calif. 94133

[21] Appl. No.: 319,032

[22] Filed: Oct. 6, 1994

[51] Int. Cl.⁶ .................................................. A61M 25/00
[52] U.S. Cl. ........................ 604/281; 604/164; 604/264
[58] Field of Search .................................. 604/164–166, 604/264, 272, 280–281, 167–170, 29, 51, 53, 158, 161

[56] References Cited

U.S. PATENT DOCUMENTS

| | | |
|---|---|---|
| 3,613,684 | 10/1971 | Sheridan . |
| 3,680,562 | 4/1972 | Wittes et al. . |
| 3,860,006 | 1/1975 | Patel . |
| 4,027,659 | 6/1977 | Slingluff . |
| 4,617,929 | 10/1986 | Gill . |
| 4,645,492 | 2/1987 | Weeks . |
| 4,883,474 | 11/1989 | Sheridan . |
| 4,986,814 | 1/1991 | Burney et al. . |
| 5,041,085 | 8/1991 | Osborne et al. . |
| 5,078,689 | 1/1992 | Keller . |
| 5,205,830 | 4/1993 | Dassa et al. . |
| 5,263,937 | 11/1993 | Shipp . |
| 5,279,551 | 1/1994 | James . |

Primary Examiner—C. Fred Rosenbaum
Assistant Examiner—Perry E. Van Over
Attorney, Agent, or Firm—Cushman Darby & Cushman

[57] ABSTRACT

A chest tube assembly is constructed and arranged for insertion into the pleural cavity and includes an elongated catheter having a proximal portion and a distal portion. A central lumen extends the length of the catheter and communicates with an open distal end. The catheter is of pre-formed shape such that a longitudinal axis of a distal segment of the distal portion forms an angle of approximately 90° with a longitudinal axis of the proximal portion of the catheter. A trocar is constructed and arranged to be slidably disposed within the central lumen to selectively project from the open distal end of the catheter. The catheter is constructed and arranged such that (1) when the trocar is disposed in the central lumen, the catheter is straightened, thereby aligning the longitudinal axis of the distal segment with the longitudinal axis of the proximal portion, and (2) when the trocar is removed from the distal portion of the catheter, the catheter bends, returning to its pre-formed shape.

15 Claims, 2 Drawing Sheets

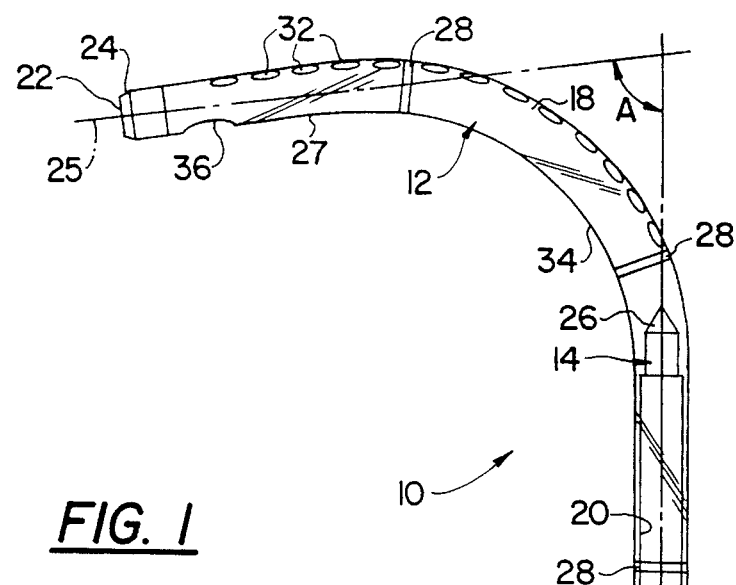
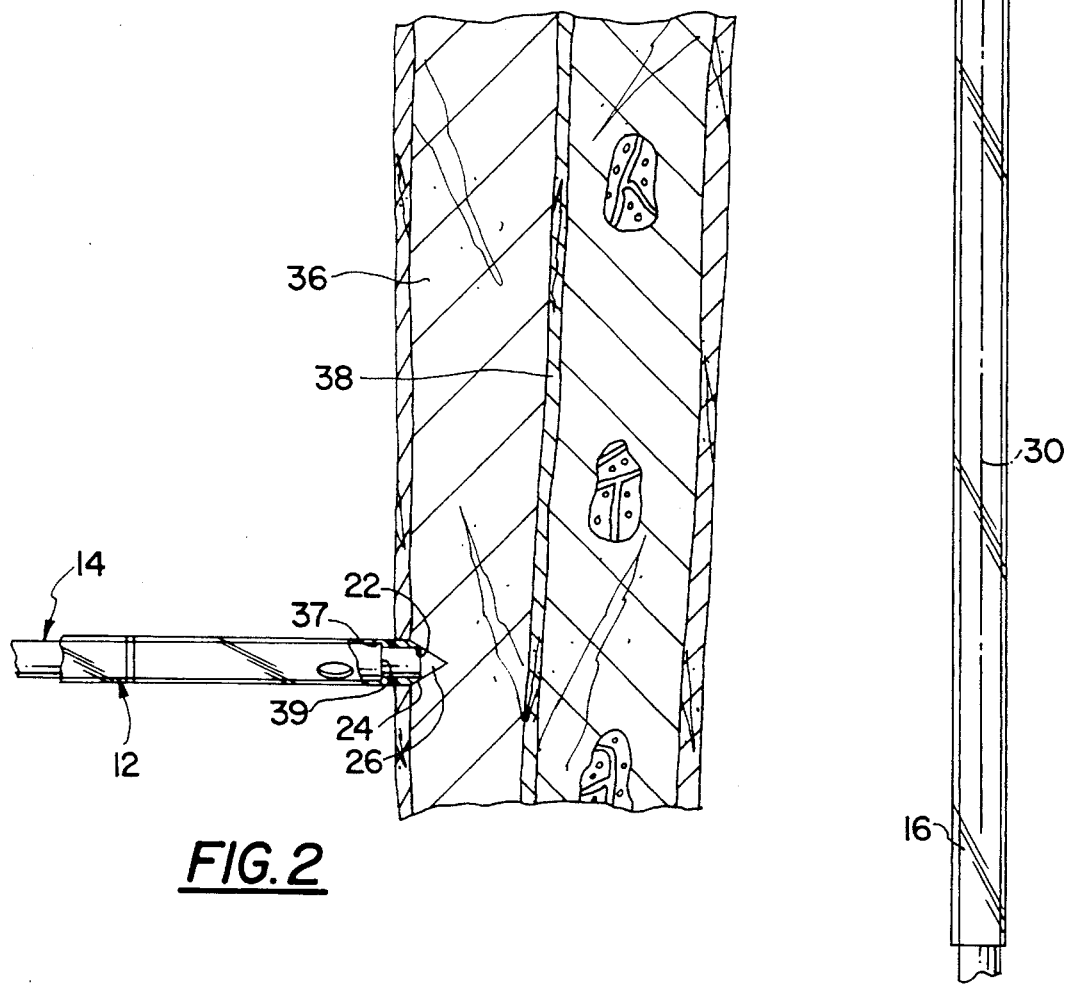
FIG. 1
FIG. 2

BENT CHEST TUBE ASSEMBLY

BACKGROUND OF THE INVENTION

This invention relates to a trocar catheter and, more particularly, to a chest tube assembly for evacuating air, fluid, or blood to allow for re-expansion of a collapsed lung and for maintaining drainage until the collapsed lung has been fully re-expanded.

Trocar catheters or chest tube assemblies have been developed for draining the pleural cavity, thereby permitting a collapsed lung to re-expand. To avoid possible damage to the patient, the chest tube assembly must be capable of insertion through the chest wall of the patient without flexing or deviation from the desired path. In addition, the penetration of the assembly must be accomplished without inflicting trauma to the expanding lung.

Conventional chest tube assemblies may be of a single element construction such as a catheter of rigid material having a pointed end for penetrating tissue. Chest tube assemblies may alternatively be in the form of a flexible, straight catheter having an axial lumen. With such catheters, a trocar is inserted through the lumen so as to selectively project from the distal end thereof. The trocar provides the catheter with sufficient rigidity during placement within the patient's body.

Notwithstanding these prior developments in the field of trocars and catheters, further improvements are needed in the construction of chest tube assemblies. Such improvements include giving the user an indication of the approximate position within the patient of the distal end of assembly, providing an improved anchoring function once the assembly is inserted into the pleural cavity, and minimizing the likelihood that drainage will be inhibited by clogging or obstruction so that proper drainage of the cavity may occur.

SUMMARY OF THE INVENTION

It is an object of the present invention to provide a trocar catheter or chest tube assembly which is configured to maximize penetration into the pleural cavity such that the likelihood of inadvertent removal of the assembly is minimized and to ensure that sufficient drainage of the cavity can occur until the collapsed lung has been fully re-expanded.

In accordance with the principles of the present invention, these objectives are obtained by providing a chest tube assembly which is constructed and arranged for insertion into the pleural cavity. The assembly includes an elongated catheter having a proximal portion and a distal portion. The catheter has a central lumen extending the length thereof and communicating with an open distal end thereof. The catheter is of a pre-formed shape such that a longitudinal axis of a distal segment of the distal portion forms an angle of approximately 90° with a longitudinal axis of the proximal portion of the catheter. A trocar is constructed and arranged to be slidably disposed within the central lumen so as to selectively project from the open distal end of the catheter. The catheter is constructed and arranged such that when the trocar is disposed in the central lumen, the catheter is straightened, thereby aligning the longitudinal axis of the distal segment with the longitudinal axis of the proximal portion, and when the trocar is removed from the distal portion of the catheter, the catheter bends, returning to its pre-formed shape.

In contrast to conventional straight catheters, the bent distal portion of the catheter provides an anchoring function, reducing the likelihood of inadvertent removal of the catheter from the pleural cavity. A plurality of drainage holes are provided in the distal portion. The catheter is constructed and arranged to be clamped to the skin such that draining of the cavity can take place. The catheter also includes indicia which confirms to the user the depth at which the assembly is inserted into the cavity, so as to prevent inadvertent damage to the lung or other tissue.

In accordance with another aspect of the present invention, a method of inserting the chest tube assembly into the pleural cavity is provided. The method includes the steps of advancing the chest tube assembly with a trocar tip projecting from an open distal end of the catheter so as to pierce the pleural wall and enter the pleural cavity. The trocar is then retracted from the distal portion of the catheter leaving the distal portion in the cavity such that upon retraction of the trocar, the catheter returns to a pre-formed, bent condition with a distal segment of a distal portion thereof forming an angle of approximately 90° with a longitudinal axis of a proximal portion of the catheter. The catheter is secured to the skin and suction is applied to the catheter so that substances to be removed from the cavity may enter the openings and be removed from the cavity through the central lumen.

Other objects, features and characteristics of the present invention, as well as methods of operation and functions of related elements of the structure, and the combination of the parts and economics of manufacture, will become more apparent upon consideration of the detailed description and appended claims with reference to the accompanying drawings, all of which form a part of the specification.

BRIEF DESCRIPTION OF THE DRAWINGS

FIG. 1 is an enlarged elevational view of a chest tube assembly provided in accordance with the invention, shown with a trocar disposed in a catheter but removed from a distal portion thereof;

FIG. 2 is an enlarged schematic illustration of the chest tube assembly of FIG. 1, shown partially in section and with the trocar projecting from a distal portion of the catheter, puncturing skin, and in position to puncture the pleural cavity;

DETAILED DESCRIPTION OF THE PRESENTLY PREFERRED EXEMPLARY EMBODIMENT

Figure 3:
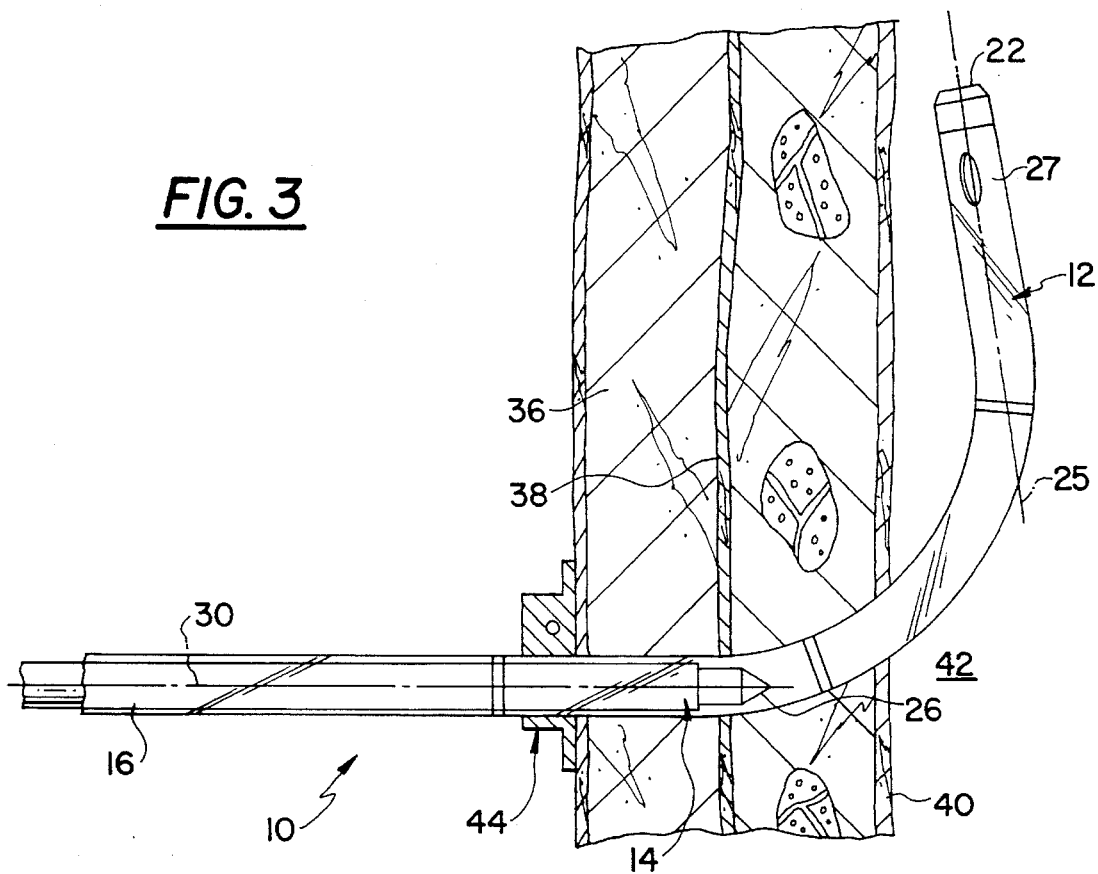
FIG. 3 is an enlarged schematic illustration of the chest tube assembly of FIG. 2, shown with a distal portion of the catheter inserted into the pleural cavity with the trocar removed from the distal portion, and with a portion of the catheter being clamped to the skin.

Referring to the drawings, a trocar catheter or chest tube assembly, generally indicated 10, which embodies the principles of the present invention, is shown.

The chest tube assembly 10 includes an elongate catheter 12 and a trocar 14. The catheter 12 has a proximal portion 16 and a distal portion 18. A central lumen 20 extends the length of the catheter 12, to the open distal end 22. The open distal end 22 defines a bevelled surface 24 which is complementary to the trocar piercing tip 26, permitting easy penetration of the chest tube assembly 10 with minimum tissue damage, as will be explained more fully below.

The catheter 12 is preferably formed from latex, teflon, silastic, polyurethane, or other suitable material. The distal portion 18 of the catheter 12 is marked with indicia 28, preferably spaced one inch apart. In the illustrated embodiment the indicia 28 comprises three annular marks on the periphery of the catheter 12. These marks are used to confirm the depth of insertion of the distal portion 18, which will become apparent below.

The catheter 12 may be provided in a variety of sizes. For example, for use in draining the pleural cavity of adults, the catheter may be approximately 26 French, and for use in children, the catheter may be in the range of 10–12 French.

The catheter is pre-formed such that a longitudinal axis 25 of a distal segment 25 of the distal portion 18 forms an angle A of generally 90° with the longitudinal axis 30 of the proximal portion 16 (FIG. 1). However, when the trocar 14 is disposed within the catheter 12 at the distal portion 18 thereof, the trocar 14 straightens the catheter 12 (FIG. 2) such that the axis 25 of the distal segment 27 aligns with the axis 30 of the proximal portion 16. Only when the trocar 14 is removed from the distal portion 18 of the catheter 12 will the catheter 12 return to its bent, pre-formed shape.

As shown in FIG. 1, the distal portion 18 includes a plurality of spaced drainage holes 32 which are approximately 0.25 inches in diameter. With reference to the bent condition of the catheter 12, the drainage holes 32 may be staggered in placement along the convex surface (FIG. 1) of the distal portion 18. The drainage holes 32 extend from the open distal end 22 to approximately the two inch indicia mark on the catheter 12. Since a plurality of drainage holes are provided, even if some of the holes become clogged with material being removed from the cavity, sufficient drainage of the cavity can still occur.

As shown in FIG. 1, a radio-opaque line 34 is provided along the concave surface of the catheter 12 and extends from the open distal end 22 to at least the distal half of the catheter 12. The radio-opaque line 34 permits the user to determine the chest tube assembly 10 location. The radio-opaque line 34 is a solid ribbon of radio opaque material such as bromide or bismuth salt.

An opening 36, communicating with the lumen 20, is disposed near the open distal end 22 of the catheter 12. The opening 36 is provided to irrigate the chest cavity or to otherwise introduce medication therethrough. The radio-opaque line 34 can be used to locate the opening 34 precisely for direct topical treatment.

As noted above, the chest tube assembly 10 also includes a trocar 14. The trocar 14 is a rigid or semirigid, elongated member, constructed and arranged to be slidably moved within the lumen 20 of the catheter 12. The trocar 14 has significantly less flexibility than the catheter 12 to maintain the rigidity of the assembly 10 as the assembly 10 is inserted into the patient.

Figure 4:
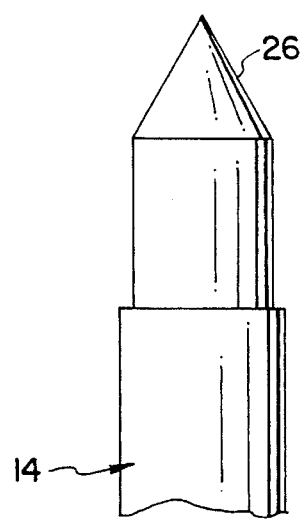
FIG. 4 is an enlarged view of a distal end of the trocar of the chest tube assembly.

The trocar tip 26 may be constructed in any desired configuration suitable for piercing tissue. In the illustrated embodiment, the trocar has a conical, pointed piercing tip which is constructed and arranged to project from the distal open end 22 of the catheter when the trocar is advanced fully, as shown in FIG. 4. When the trocar is advanced fully, stop surface 39 of the trocar 14 engages stop 37 of the catheter 12. In this position, the trocar tip 26 aligns with the bevelled surface 24 of the catheter 12 to allow smooth and easy penetration of tissue, and thus, minimize tissue damage.

The placement of the chest tube assembly 10 into the pleural cavity can be appreciated with reference to FIGS. 1–3. As shown in FIG. 2, the trocar 14 is inserted into the catheter 12 thereby straightening the distal portion 18 thereof. The chest tube assembly 10 with the trocar tip 26 projecting from the distal portion 18 of the catheter 12, is then brought to the location of the cavity to be drained. The insertion of the chest tube assembly 10 can be performed easily in a few minutes. First, the skin and the intercostal space are infiltrated with a local anesthetic solution. Next a small incision, slightly smaller than the trocar tip 26 to prevent air leakage, is made. The trocar 14 can be advanced with a rotary motion through the skin and subcutaneous tissue 36, the intercostal space 38, and through the pleura 40 to enter the pleural cavity 42. Once the cavity 42 is entered, the trocar 14 can be withdrawn to prevent possible lung damage. When the trocar 14 has been retracted approximately three inches beyond the open distal end 22 of the catheter 12, as indicated by the third indicia mark, the distal portion 18 of the catheter will automatically bend to its pre-formed position as shown in FIG. 3. Thus, the longitudinal axis 25 of the distal segment 27 is disposed approximately 90° with respect to the longitudinal axis 30 of the proximal portion 16. Further insertion of the catheter 12 will place the bent 90° distal segment 27 tangentially against the pleura wall 40. Complete withdrawal of the trocar 14 completes the placement of the catheter 12.

Figure 5:
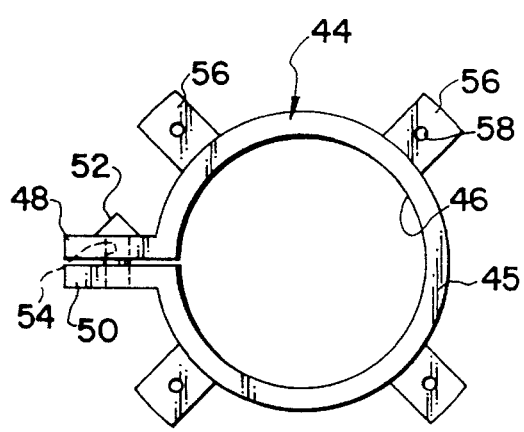
FIG. 5 is an enlarged plan view of a clamp assembly for securing the chest tube assembly to skin.

The catheter 12 is clamped via a clamp assembly, generally indicated at 44, which is sutured or taped onto the skin. As shown in FIG. 5, the clamp assembly 44 includes a slit ring member 45 having an inner diameter portion 46 which is constructed and arranged to surround the outer diameter of the catheter 12. First and second opposing leg members 48, 50 extend from the ring member 45 for locking the clamp assembly 44. The second leg member 50 includes a protrusion 52 which is constructed and arranged to snap into a bore 54 defined in the first leg member 48, thereby locking the clamp assembly 44 about the periphery of the catheter 12. The clamp assembly 44 can be sutured or taped to the skin via segments 56 which extend radially outwardly and include a bore 58 therethrough.

After securing the catheter 12, suction may then be applied to the open distal end 22 thereof to produce the required suction evacuation. Since the distal portion 18 is in a bent condition, a significant length of the catheter 12 can be introduced into the cavity, reducing the likelihood of inadvertent removal of the catheter from the cavity. Further, by providing a plurality of drainage holes 32 in the distal portion 18 of the catheter 12, proper drainage can take place even if some of the holes become occluded with the material being drained.

The catheter 12 can be removed easily by simultaneously extracting the catheter, applying a vaseline impregnated gauze or the like over the skin hole, covering the hole with added gauze and thereafter taping the gauze in position.

It can be seen at the chest tube assembly 10 of the invention provides an easy and effective way of draining the pleural cavity while ensuring that the catheter will not be removed inadvertently from the cavity.

While the invention has been described in connection with what is presently considered to be the most practical and preferred embodiment, it is understood that the invention is not limited to the disclosed embodiment, but, on the contrary, it is intended to cover various modifications and equivalent arrangements included within the spirit and scope of the appended claims.

What is claimed is:

1. A chest tube assembly constructed and arranged for insertion into the pleural cavity, comprising:

an elongated catheter having a generally straight proximal portion and a generally straight distal portion, said catheter having a central lumen extending the length thereof and communicating with an open distal end thereof, said catheter being of pre-formed shape such that, when free from external forces, a longitudinal axis of said distal portion forms an angle of approximately 90° with a longitudinal axis of the proximal portion of the catheter; and a trocar constructed and arranged to be slidably disposed within said central lumen to selectively project from said open distal end of said catheter, said catheter being constructed and arranged such that (1) when said trocar is disposed in said central lumen, said catheter is straightened, thereby aligning the longitudinal axis of said distal portion with the longitudinal axis of the proximal portion, and (2) when said trocar is removed from said distal portion of said catheter, said catheter bends, returning to said pre-formed shape.

2. The chest tube assembly as defined in claim 1, wherein said catheter is made of flexible material having a stiffness less than the stiffness of the trocar.

3. The chest tube assembly according to claim 1, wherein said distal portion includes a plurality of openings therein communicating with said lumen, said openings being defined in a convex surface of said catheter when said distal portion thereof is in its bent, pre-formed shape.

4. The chest tube assembly according to claim 3, wherein said catheter includes a radio-opaque line disposed on a surface thereof opposite said openings and extending toward the proximal portion of the catheter.

5. The chest tube assembly according to claim 1, wherein said distal portion includes indicia thereon for indicating an insertion depth of said catheter.

6. The chest tube assembly according to claim 2, wherein the catheter is made from material selected from the group consisting of latex, teflon, silastic, and polyurethane.

7. The chest tube assembly according to claim 4, wherein said radio opaque line comprises one of bromide and bismuth salt.

8. The chest tube assembly according to claim 1, wherein said catheter is approximately 26 French.

9. The chest tube assembly according to claim 1, wherein said catheter is in the range of 10–12 French.

10. The chest tube assembly according to claim 1, wherein said distal open end of the catheter defines a bevelled surface which aligns with a distal tip of the trocar when the trocar is advanced fully into the catheter.

11. The chest tube assembly according to claim 10, wherein said trocar includes a stop surface which engages with a stop defined in said catheter when said trocar is advanced fully into the catheter.

12. The chest tube assembly according to claim 3, wherein said openings are spaced apart and are approximately 0.25 inches in diameter.

13. The chest tube assembly according to claim 3, wherein the distal portion is approximately three inches in length, said openings being disposed approximately two inches from the open distal end of the catheter.

14. A chest tube assembly and clamp assembly combination, the chest tube assembly being constructed and arranged for insertion into the pleural cavity and comprising:

an elongated catheter having a proximal portion and a distal portion, said catherter having a central lumen extending the length thereof and communicating with an open distal end thereof, said catheter being of pre-formed shape such that a longitudinal axis of a distal segment of said distal portion forms an angle of approximately 90° with a longitudinal axis of the proximal portion of the catheter; and a trocar constructed and arranged to be slidably disposed within said central lumen to selectively project from said open distal end of said catheter, said catheter being constructed and arranged such that (1) when said trocar is disposed in said central lumen, said catheter is straightened, thereby aligning the longitudinal axis of said distal segment with the longitudinal axis of the proximal portion, and (2) when said trocar is removed from said distal portion of said catheter, said catheter bends, returning to said pre-formed shape, and said clamp assembly including a split ring member constructed and arranged to surround a periphery of said catheter, said ring member including leg members for locking said clamp assembly to said catheter, said ring member including a plurality of segments extending radially therefrom for securing the clamp assembly to skin.

15. A method for draining the pleural cavity with a chest tube assembly, the chest tube assembly including a catheter having a proximal portion, a distal portion having a distal segment terminating in an open distal end and a central lumen communicating with said open distal end, a plurality of openings being defined in the distal portion of the catheter, said catheter having a bent, pre-formed shape such that a longitudinal axis of the distal segment forms an angle of approximately 90° with a longitudinal axis of said proximal portion; and a trocar having a piercing tip and being slidably disposed within said central lumen and selectively projecting from said open distal end, the method comprising the steps of:

introducing the trocar into the central lumen thereby straightening the catheter by aligning the longitudinal axis of the distal segment with the longitudinal axis of the proximal portion, advancing the chest tube assembly with said trocar tip projecting from said open distal end of said catheter so as to pierce the pleural wall and enter the pleural cavity, retracting said trocar from the distal portion of said catheter leaving said distal portion in said cavity such that upon retraction of said trocar, said catheter returns to its bent, pre-formed shape, securing a portion of said catheter to skin, and applying suction to the catheter so that substances to be removed from the cavity may enter the openings and be removed from the cavity through the central lumen.

\* \* \* \* \*